United States Patent [19]

Haag et al.

[11] 4,329,509
[45] May 11, 1982

[54] CO-PRODUCTION OF 2-ALKANONES AND PHENOLS

[75] Inventors: Werner O. Haag, Lawrenceville; Lewis B. Young, Skillman, both of N.J.

[73] Assignee: Mobil Oil Corporation, New York, N.Y.

[21] Appl. No.: 227,339

[22] Filed: Jan. 22, 1981

Related U.S. Application Data

[63] Continuation of Ser. No. 99,344, Nov. 30, 1979, abandoned.

[51] Int. Cl.$^3$ .................... C07C 45/53; C07C 37/08
[52] U.S. Cl. .................................. 568/385; 568/342; 568/311; 568/798; 568/768; 585/455
[58] Field of Search ............... 568/342, 385, 311, 798, 568/768, 794, 786, 804; 585/455

[56] References Cited

U.S. PATENT DOCUMENTS

| | | | |
|---|---|---|---|
| 2,874,193 | 2/1959 | Dijkstra | 260/624 |
| 3,251,897 | 5/1966 | Wise | 260/671 |
| 3,474,154 | 10/1969 | Yamanaka et al. | 260/671 |
| 3,706,807 | 12/1972 | Etherington et al. | 260/624 |
| 3,728,408 | 4/1973 | Tobias | 260/668 C |
| 3,755,483 | 8/1973 | Burress | 260/671 R |
| 3,872,173 | 3/1975 | Berthoux et al. | 260/624 E |
| 3,876,710 | 4/1975 | Saito et al. | 260/624 C |
| 3,962,364 | 6/1976 | Young | 260/671 C |
| 3,992,455 | 11/1976 | Leston | 260/619 R |
| 4,016,218 | 4/1977 | Haag et al. | 260/671 R |
| 4,197,413 | 4/1980 | Kaeding et al. | 568/798 |

FOREIGN PATENT DOCUMENTS

| | | |
|---|---|---|
| 1150209 | 4/1967 | United Kingdom . |
| 1132859 | 11/1968 | United Kingdom . |
| 1496227 | 12/1977 | United Kingdom . |
| 185930 | 10/1966 | U.S.S.R. . |
| 352868 | 10/1972 | U.S.S.R. . |
| 539021 | 12/1976 | U.S.S.R. . |

OTHER PUBLICATIONS

Venuto et al.; *Journal of Catalysis*, vol. 4, pp. 81-98 (1966).

Primary Examiner—Natalie Trousof
Assistant Examiner—James H. Reamer
Attorney, Agent, or Firm—Charles A. Huggett; Ronald J. Cier; George W. Allen

[57] ABSTRACT

A process for the co-production of 2-alkanones having at least five carbon atoms and phenol or a substituted phenol. In the first step, benzene or a substituted benzene is alkylated with an alkyl moiety of at least five carbon atoms to selectively produce the 2-arylalkane isomer. Subsequent oxidation to the hydroperoxide and acid cleavage thereof yields the desired product. The alkylation step is carried out in the presence of a novel class of selective crystalline zeolite materials having pore openings with a major dimension of six to seven angstroms.

11 Claims, No Drawings

CO-PRODUCTION OF 2-ALKANONES AND PHENOLS

This is a continuation of application Ser. No. 099,344 filed Nov. 30, 1979 now abandoned.

BACKGROUND OF THE INVENTION

1. Field of the Invention

This invention is directed to a process for the production of oxygenated organic compounds. In particular, it is concerned with the selective production of 2-alkanones and phenols by a process utilizing a novel class of crystalline zeolite catalysts.

2. Description of the Prior Art

The relatively long chain 2-alkanones, i.e. those having five or more carbon atoms in the primary chain, are generally prepared by complex multistep processes or in a reaction which leads to a mixture of products, such as:

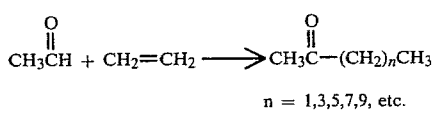

$$n = 1,3,5,7,9, \text{etc.}$$

Phenols are traditionally prepared by the oxidation of alkylbenzenes (e.g. isopropylbenzene) and the acid catalyzed rearrangement of the resultant hydroperoxide to the corresponding phenol and ketone. For example:

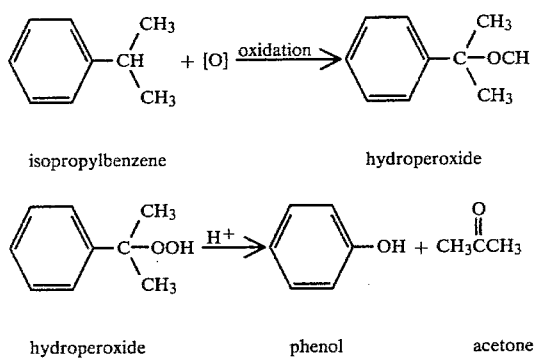

2-Alkanones are useful in the agricultural arts as herbicides. For instance, 2-dodecanone is known to be an effective cotton defoliant. Other 2-alkanones are useful as chemical intermediates. Phenol is a large volume chemical product which is used to manufacture various resins. Methyl substituted phenols are also produced commercially in relatively large volume.

SUMMARY OF THE INVENTION

We have now discovered a novel and convenient method for co-producing relatively long chain length 2-alkanones and phenol or substituted phenol. In the first step, benzene or a substituted benzene is alkylated with an alkylating agent (e.g. an olefin) having at least five carbon atoms. The alkylation reaction is carried out in the presence of a member of a novel class of shape selective crystalline zeolite catalysts, the catalyst affecting the reaction such that the resultant alkylbenzene product is rich in the 2-arylalkane isomer.

The crystalline zeolite catalysts which comprise the hereinuseful novel class of shape selective zeolites are characterized by crystal structures having channels or networks of pores therethru, the major dimension of the openings to such channels or pores being between about 6 and 7 angstrom units. Specific preferred members of this class include cancrinite, gmelinite, mordenite, and offretite, as well as synthetic and naturally occurring isotypes thereof. A particularly preferred zeolite, the crystallographic structure of which is unknown at the present time, is the synthetic zeolite ZSM-12.

In the second step of our process, the alkylation product of the above-described first step is oxidized to a hydroperoxide. The hydroperoxide is thereafter subjected to acid-catalyzed rearrangement (the third step) to yield the desired 2-alkanone having the same number of carbon atoms as the alkylating agent originally utilized, together with the phenolic compound. Both the second and third steps utilize conventional technology such as is used, for example, in the co-production of acetone and phenol from isopropylbenzene.

DESCRIPTION OF SPECIFIC EMBODIMENTS

It is contemplated that alkylating agents useful in the process of this invention will include any aliphatic or aromatic organic compound, having one or more available alkyl groups of at least five carbon atoms, which are capable of reacting with an aromatic compound. Useful alkylating agents include, for example, alkyl halides, olefins or alcohols having a linear hydrocarbon chain length or "backbone" of at least five (5) carbon atoms, and preferably from about 6 to about 20 carbon atoms. Olefins are the preferred alkylating agents, although one may plainly substitute any other hydrocarbon material which will generate unsaturated carbon atoms in the presence of the disclosed alkylation catalysts.

The aromatic compounds which are to be reacted with the foregoing alkylating agents to yield 2-phenylalkanes by the process disclosed herein are benzene compounds. These benzene compounds may be unsubstituted, or they may carry from 1 to 2 substituents on the ring structure. If substituted, the substituent may be an alkyl group having from 1 to 10 carbon atoms therein, or may be a halide, an alkoxy, an aryl group, and so forth, or any combination of such substituents.

The zeolites utilized in the first step of the novel process may be either naturally occurring or synthetic and include, by way of example: cancrinite, gmelinite, mordenite, dealuminized mordenite, offretite and ZSM-12. Also contemplated as being included in this novel class of shape selective zeolites are synthetic and naturally occurring isotypes of such zeolite materials, such as: zeolite S, zeolite Na-S, zeolite Na-D, Ptilolite, Zeolon, zeolite O, TMA-offretite, and others.

The crystal structure of the class of zeolites suitable for use as catalysts in the process of this invention is such as to provide access to and egress from the intracrystalline free space of the zeolites by virtue of having channels or networks of pores (hereinafter referred to as pores) therethru, the openings of such pores preferably having a major dimension of between about 6 Å and about 7 Å. The zeolites utilized herein are further characterized by pore apertures of about a size as would be provided by 12-member rings of silicon or aluminum atoms. It will be understood, of course, that these rings are those formed by the regular disposition of the tetrahedra making up the anionic framework of the crystalline zeolite, the silicon or aluminum atoms forming the centers of the tetrahedra and being themselves bonded together by oxygen atoms.

The pores characterizing the zeolites useful in the present process may be substantially circular, such as is the situation with respect to cancrinite which has substantially uniform pores of about 6.2 angstroms in diameter, or may be somewhat elliptical, such as in mordenite which has pores of approximately 6.7 by 7.0 angstroms. It should be understood that, in any case, the zeolites used as catalysts in the process of this invention have a major pore dimension intermediate between that of the large pore zeolites, such as the X and Y zeolites, and the relatively small pore size zeolites ZSM-5 and ZSM-11, and preferably between about 6 A and about 7 A. With the exception of zeolite ZSM-12, the pore size dimensions and crystal structures of the above zeolites are substantially those specified in ATLAS OF ZEOLITE STRUCTURE TYPES by W. M. Meier and D. H. Olson, published by the Structure Commission of the International Zeolite Association (1978) and distributed by Polycrystal Book Service, Pittsburgh, Pa.

ZSM-12, the structure and pore size of which are unknown at the present time, is described in U.S. Pat. No. 3,832,449. That description, and in particular the characteristic crystal X-ray diffraction pattern disclosed therein, is incorporated herein by reference.

The zeolites useful in the novel process of this invention generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g. ammonium ions, which upon calcination yield the hydrogen form. This exchange is conveniently carried out by contact of the zeolite with an ammonium salt solution, e.g. ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

An especially useful modifying treatment entails steaming of the zeolite by contact with an atmosphere containing from about 5 to about 100 percent steam at a temperature of from about 250° to 1000° C. Steaming may last for a period of between about 0.25 and about 100 hours and may be conducted at pressures ranging from sub-atmospheric to several hundred atmospheres to reduce the alpha value of the zeolite to less than 500, and preferably less than 20, but greater than zero.

In practicing the desired conversion process, it may be useful to incorporate the above-described intermediate pore size crystalline zeolites in another material resistant to the temperature and other conditions employed in the process. Such matrix materials include synthetic or naturally occurring substances as well as inorganic materials such as clay, silica, and/or metal oxides. The latter may be either naturally occurring or in the form of gels or gelatinous precipitates, including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment, or chemical modification.

In addition to the foregoing materials, the intermediate pore size zeolites employed herein may be compounded with a porous matrix material, such as alumina, silica-alumina, silica-magnesia, silica-zironia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely, with the zeolite content ranging from between about 1 to about 99 percent by weight and more usually in the range of about 5 to about 80 percent by weight of the composite.

The process of this invention comprises what is basically a three-step reaction. In Step 1 the aforementioned aryl compound and alkylating agent are reacted in the presence of a member of the novel class of shape selective zeolites to yield the 2-arylalkane isomer. Step 2 is an oxidation step wherein the 2-arylalkane is oxidized with a suitable oxidizing agent to produce the corresponding hydroperoxide. In Step 3 the hydroperoxide is cleaved and rearranged in the presence of an acid catalyst to yield the 2-alkanone of the same carbon chain length as the cleaved alkyl group and also a phenol based on the structure of the aryl moiety.

The process shall be further described and illustrated with the aid of some examples.

STEP 1—Alkylation

The first (i.e. alkylation) step of the process is conducted such that the organic reactants, i.e. the aromatic compound and the alkylating agent, are brought into contact with the selective zeolite in a suitable reaction zone, such as a fixed bed of the catalyst, under effective alkylation conditions. Such conditions include a temperature of between about 50° C. and about 500° C., a pressure of between about $2.5 \times 10^4$ N/m$^2$ and about $2.5 \times 10^7$ N/m$^2$ (0.25–250 atmospheres) and, when flow systems are contemplated, a feed weight hourly space velocity (WHSV) of between about 0.1 and about 500. The latter WHSV is based upon the weight of the catalyst compositions employed, i.e. the total weight of active catalyst and binder therefor. Preferred reaction conditions include a temperature within the approximate range of 100° C. to 350° C. with a feed WHSV of between 0.5 and 100. Although the reaction normally takes place at atmospheric pressure ($10^5$ N/m$^2$), the preferred pressure range extends from about $10^5$ N/m$^2$ to about $5 \times 10^6$ N/m$^2$. The reactants may be in either the vapor phase or the liquid phase and may be neat, i.e. free from intentional admixture or dilution with other material, or may be brought into contact with the zeolite with the aid of carrier gases or diluents such as, for example, hydrogen or nitrogen.

The alkylation step described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The catalyst, after use, is preferably conducted to a regeneration zone where coke is burned from the used catalyst in an oxygen-containing atmosphere (such as air) at elevated temperature, after which the regenerated catalyst is recycled to the conversion zone for further contact with the organic reactants.

The following examples are provided to illustrate Step 1 of the process of this invention and to aid those in the art in the understanding thereof, but clearly should not be taken as presenting undue limitations thereon:

EXAMPLE 1

(ZSM-12)

Benzene was alkylated with octene-1 in the presence of zeolite HZSM-12 (silica/alumina ratio=90; 65 wt. % on alumina binder). The reaction was carried out in a flow reactor at 205° C. and 200 psig. The reactants, at a benzene/octene mole ratio of 4/1, were passed across the catalyst at a feed WHSV of 30 hr$^{-1}$. Analysis of the effluent indicated that, at 99% octene-1 conversion, selectivity to phenyloctane was 53%. Composition of the phenyloctanes was: 92% 2-phenyloctane, 7% 3-phenyloctane, and 1% 4-phenyloctane, with 69% being linear phenyloctanes.

EXAMPLE 2

($AlCl_3$)

Using conventional Friedel-Crafts technology, benzene and octene-1 (mole ratio 8/1) were reacted with $AlCl_3$ catalyst at 30° C. and atmospheric pressure. Octene-1 conversion was 97% and selectivity to phenyloctane 73%. Isomeric composition of the phenyloctane was: 49% 2-phenyloctane, 28% 3-phenyloctane, and 23% 4-phenyloctane, with 100% thereof being linear phenyloctanes.

EXAMPLE 3

(Mordenite, dealuminized)

A sample of mordenite (Norton Zeolon Type 100 H, silica/alumina mole ratio=10) was air calcined for one hour at 400° C. followed by one hour at 600° C. The material was refluxed for 20 hours with 0.5 N HCl (50 ml of solution per gram of zeolite) and then refluxed for 20 hours with distilled water. The silica to alumina ratio of the resulting dealuminized mordenite was 93.

Benzene and octene-1 (mole ratio=4/1) were passed over a sample of the above material at a feed WHSV of 30 hr$^{-1}$, 198° C. and 200 psig. Conversion of the $C_8=$ was 100% with 76% selectivity to phenyloctanes. Isomeric composition of the phenyloctanes was: 71.7% 2-phenyloctane, 28.3% 3-phenyloctane, and no detectable amount of 4-phenyloctane; 87% of the phenyloctane product was linear phenyloctanes.

EXAMPLE 4

(Mordenite, dealuminized)

Repeat of Example 3, except at a temperature of 155° C., pressure of 210 psig and WHSV=90 hr$^{-1}$. Octene conversion was 99.3% and selectivity to phenyloctane 77%. Isomeric phenyloctane composition was: 86.6% 2-phenyloctane, 13.4% 3-phenyloctane, and no detectable amount of 4-phenyloctane; 96% of the phenyloctanes were linear.

EXAMPLE 5

(ZSM-12, steamed)

A sample of the same HZSM-12 as was used in Example 1 was steamed prior to use by passing steam over the catalyst at a pressure of one atmosphere (absolute) at 538° C. for about seven hours. A benzene/octene-1 feed stream (mole ratio=8/1) was passed over the steamed catalyst at 194° C., 565 psig and WHSV of 30 hr$^{-1}$. Conversion of octene was 88% with 83% selectivity to phenyloctane. The phenyloctane composition was as follows: 93% 2-phenyloctane, 6% 3-phenyloctane, and 1% 4-phenyloctane; 81% linear phenyl-substituted octanes.

EXAMPLE 6

(ZSM-11)

A sample of synthetic zeolite HZSM-11 (U.S. Pat. No. 3,709,979), which has a major pore dimension of 5.5 A, was placed in a flow reactor at 256° C. A feed stream of benzene and octene-1 (mole ratio=4/1) was passed over the catalyst at 615 psig and a WHSV of 30 hr$^{-1}$. Conversion of octene-1 was 100%, but selectivity to phenyloctane was only 6%. Due to the low yield and the large number of products found, the isomeric phenyloctanes could not be positively identified.

As will be seen from the foregoing, zeolite catalysts within the scope of those utilizable in Step 1 of the present invention—i.e. ZSM-12 and mordenite—are shown to selectively produce 2-phenyloctane in preference to the 3- and 4-isomers, as compared to the conventional $AlCl_3$ catalyst. Conversion rates were high and the yield of the linear product excellent. Zeolite HZSM-11, which has a pore opening of less than the desired 6 to 7 angstroms, is shown to have poor selectivity to phenyloctanes in general.

EXAMPLES 7-14

In a series of runs utilizing various zeolite materials, benzene was alkylated with dodecene-1. The feed stream was a 4/1 mole ratio mixture of benzene and dodecene-1 which was passed across each of the catalysts at WHSV of 30 hr$^{-1}$. The reaction temperatures and pressures are shown in Table I below, as are the level of $C_{12}=$ conversion and the selectivity to phenyldodecane. Table II summarizes the isomeric distribution of the phenyldodecane produced.

TABLE I

| | Catalyst comparison - Benzene + Dodecene-1 | | | | | |
|---|---|---|---|---|---|---|
| Example | Zeolite | Major Pore Dimension | Temp. | Pressure | $C_{12}=$ Conversion | Selectivity to $\phi$-$C_{12}$ |
| 7 | HZSM-12 | * | 200° C. | 190 psig | 54% | 63% |
| 8 | Mordenite** | 7.0A | 200° C. | 200 psig | 98% | 80% |
| 9 | Offretite | 6.4A | 250° C. | 620 psig | 97% | 73% |

TABLE I-continued

Catalyst comparison - Benzene + Dodecene-1

| Example | Zeolite | Major Pore Dimension | Temp. | Pressure | $C_{12}=$ Conversion | Selectivity to $\phi$-$C_{12}$ |
|---|---|---|---|---|---|---|
| 10 | HZSM-4 | 7.4A | 205° C. | 210 psig | 92% | 73% |
| 11 | Beta | * | 250° C. | 600 psig | 38% | 47% |
| 12 | Linde L | 7.1A | 195° C. | 210 psig | 72% | 72% |
| 13 | HZSM-38 | * | 200° C. | 215 psig | 94% | 73% |
| 14 | REY | 7.4A | 200° C. | 220 psig | 89% | 85% |

NOTES:
*Pore size unknown.
**Dealuminized, see Example 3.

TABLE II

Catalyst Comparison - Phenyldodecane Isomer Distribution

| Example | Catalyst | 2-$\phi$ | 3-$\phi$ | 4-$\phi$ | 5-$\phi$ | 6-$\phi$ | % Linear |
|---|---|---|---|---|---|---|---|
| 7 | HZSM-12 | 92% | 8% | 0 | 0 | 0 | 78% |
| 8 | Mordenite (-Al) | 85% | 15% | 0 | 0 | 0 | 95% |
| 9 | Offretite | 79% | 14% | 5% | 1% | 1% | 75% |
| 10 | HZSM-4 | 57% | 25% | 8% | 5% | 5% | 90% |
| 11 | Beta | 57% | 18% | 10% | 7% | 8% | 53% |
| 12 | Linde L | 40% | 18% | 16% | 15% | 11% | 88% |
| 13 | HZSM-38 | 37% | 19% | 13% | 14% | 16% | 78% |
| 14 | REY | 25% | 20% | 18% | 19% | 18% | 92% |

The zeolites of Examples 7-9, which come within the scope of those disclosed as being utilizable in Step 1 of the present invention, are seen to selectively produce the 2-phenyldodecane isomer in very high yields with little or none of the other isomers produced as side-products. In contrast, the larger pore size zeolites of Examples 10-14 are seen to produce a relatively broader spectrum of phenyldodecane isomers, making the 2-isomer difficult to isolate in significant amounts.

STEP 2—Oxidation

Both the oxidation of the 2-arylalkane to the corresponding hydroperoxide (Step 2) and the subsequent acid-catalyzed rearrangement of the resultant hydroperoxide (Step 3) are analagous to the well-known process for the manufacture of phenol from isopropylbenzene. The conventional technology used in that process is essentially the same as that utilized herein. See, for instance, the article entitled "Phenol" in the Kirk-Othmer ENCYCLOPEDIA OF CHEMICAL TECHNOLOGY, 2nd. edition, Vol. 15, p. 147 and INDUSTRIAL CHEMICALS, 4th. edition, p. 612, by Faith, Keyes & Clark.

The oxidation reaction may be conveniently carried out either in batch or continuous operation at from about 75° C. up to about 130° C. and at pressures ranging up to about $10^6$ N/m² (10 atm.). An appropriate base, preferably in aqueous solution, is used to maintain the pH of the reaction mixture at 7 to 9 to prevent decomposition of the hydroperoxide. It is also desirable to add a radical initiator to the reaction mix to optimize the conversion rate and selectivity to the desired hydroperoxide. Suitable radical initiators are well-known and the most preferable would be an organic hydroperoxide, particularly the same aromatic hydroperoxide which is the desired product of the reaction. However, numerous other conventional radical initiators may suitably be employed (e.g. metal oxide catalysts such as $MnO_2$). The source of oxygen for the formation of the hydroperoxide is normally an oxygen-containing gas (e.g. pure $O_2$ or air) which is brought into contact with the organic reactants by convenient means, such as continuously bubbling the gas through the reaction mixture under reaction conditions.

STEP 3—Rearrangement

After formation of the hydroperoxide, it is cleaved and rearranged to the aromatic alcohol by bringing it into contact with an inorganic acid, such as $H_2SO_4$, and preferably at elevated temperature. Alternatively, the hydroperoxide, in suitable solvent, may be converted to the aromatic alcohol by means of a cation exchange resin.

Prior to carrying out the arrangement, it is preferable that the hydroperoxide be separated from the crude reaction product mix, thereby enabling one to maximize the efficiency of the cleavage reaction and also to recycle the unreacted starting materials to increase the yield and efficiency of the hydroperoxidation step. One suitable method of recovering the hydroperoxide would be by crystallization from the crude product mix, but the preferred method comprises extraction with an aqueous base (e.g. NaOH) followed by treatment of the salt with $CO_2$ to regenerate the hydroperoxide.

Recycling of the unreacted starting materials, particularly after extraction of the hydroperoxide product, is preferred, especially in continuous operations. However, such recycling may result in an accumulation of essentially inert by-products which will act as diluents and thereby prove detrimental to the reaction. It is therefore of benefit to minimize the accumulation of undesirable by-products by withdrawing a portion of the recycle prior to returning it to the oxidation reactor. Another method of preventing or minimizing accumulation of by-products would be to conduct the oxidation process in a cascade consisting of several reactors.

Oxidation and rearrangement of the 2-arylalkane cleanly produces the 2-alkanone and phenol. If the alkylating agent used in Step 1 was of a single molecular weight, then the 2-alkanone produced is likewise expected to be of a single molecular weight. When alkylating agents of varying molecular weight are employed, then a mixture of 2-alkanones results. Surprisingly, when alkylating agents of the same molecular weight but differing in the position of the expected reactive site (e.g. the position of the double bond in an olefin) are utilized in Step 1, a single 2-arylalkane isomer, and subsequently a single 2-alkanone, are the predominant reaction products in Steps 1 and 3, respectively. The phenol produced will have substantially the same aromatic structure, including original substituents, as the aromatic compound used in Step 1, except with the addition thereto of the phenolic hydroxyl group.

Having thus described the present invention with the aid of certain specific examples thereof, it is to be understood that such examples are intended to be merely illustrative of the disclosed process. Many variations thereon may be made without departing from the spirit of the disclosed invention, as will be evident to those skilled in the art, and such obvious variations are, of course, intended to come within the scope of the following claims.

We claim:

1. A method for co-producing 2-alkanones of at least five carbon atoms and phenolic compounds, said method comprising
   (A) producing arylalkane compounds enriched in the 2-arylalkane isomer, wherein the alkyl moiety has at least five carbon atoms therein, by a process comprising:
      (i) reacting an aromatic compound with an alkylating agent in the presence of a selective crystalline zeolite material, said alkylating agent comprising an aliphatic or aromatic organic compound having one or more available reactive alkyl groups of at least five carbon atoms in the linear hydrocarbon chain and said selective crystalline zeolite being characterized by a crystal structure having channels or networks of pores therethru, the major dimension of the openings to such channels or pores being between about six and about seven angstroms;
      (ii) said reaction being carried out at a temperature of between about 50° C. and about 500° C. and a pressure within the approximate range of $2.5 \times 10^4$ N/m² to $2.5 \times 10^7$ N/m²;
   (B) oxidizing said 2-arylalkane isomer with an oxidizing agent to produce the hydroperoxide thereof; and
   (C) cleaving and rearranging said hydroperoxide by contacting said hydroperoxide with an inorganic acid or a cation exchange resin to yield a 2-alkanone of substantially the same carbon chain length as the alkyl moiety and a phenolic compound.

2. A method as described in claim 1 wherein said alkyl moiety has between about six and about twenty carbon atoms in the linear hydrocarbon chain.

3. A method as described in claim 1 wherein said aromatic compound is benzene.

4. A method as described in claim 1 wherein said aromatic compound comprises a benzene ring having from one to two substituents thereon.

5. A method as described in claim 1 wherein said alkylation reaction of Step (A)(i) is carried out at a temperature within the approximate range of from 100° C. to 350° C. and a pressure of between about $10^5$ N/m² and $5 \times 10^6$ N/m².

6. A method as described in claim 1 wherein said selective zeolite is chosen from the group consisting of: cancrinite, gmelinite, mordenite, offretite, ZSM-12 and synthetic and naturally occurring isotypes thereof.

7. A method as described in claim 1 wherein said selective zeolite has the crystal structure of mordenite.

8. A method as described in claim 1 wherein said selective zeolite has the crystal structure of offretite.

9. A method as described in claim 1 wherein said selective zeolite has the crystal structure of ZSM-12.

10. A method as described in claim 1 wherein said zeolite is steamed prior to use.

11. A method as described in claim 1, 6, 7, 8, 9 or 10 wherein said zeolite is combined with a binder therefor.

* * * * *